United States Patent
Petrova et al.

(10) Patent No.: US 9,388,186 B2
(45) Date of Patent: Jul. 12, 2016

(54) PREPARATION OF CRYSTALLINE FORMS OF DIHYDROPYRAZOLOPYRIMIDINONE

(71) Applicant: Merck Sharp & Dohme Corp., Rahway, NJ (US)

(72) Inventors: Rositza Petrova, Piscataway, NJ (US); Eric Sirota, Lucerne (CH); Robert Wenslow, Cream Ridge, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 105 days.

(21) Appl. No.: 14/199,653

(22) Filed: Mar. 6, 2014

(65) Prior Publication Data

US 2014/0187562 A1 Jul. 3, 2014

Related U.S. Application Data

(63) Continuation of application No. 13/496,014, filed as application No. PCT/US2010/047622 on Sep. 2, 2010, now Pat. No. 8,703,779.

(60) Provisional application No. 61/242,428, filed on Sep. 15, 2009, provisional application No. 61/323,045, filed on Apr. 12, 2010.

(51) Int. Cl.
*A61K 31/497* (2006.01)
*C07D 487/04* (2006.01)
*A61K 31/675* (2006.01)
*A61K 31/70* (2006.01)

(52) U.S. Cl.
CPC ............ *C07D 487/04* (2013.01); *A61K 31/497* (2013.01); *A61K 31/675* (2013.01); *A61K 31/70* (2013.01)

(58) Field of Classification Search
CPC ............................ A61K 31/497; C07D 487/04
See application file for complete search history.

(56) References Cited

U.S. PATENT DOCUMENTS

2005/0350846    11/2005    Booth et al.

FOREIGN PATENT DOCUMENTS

| WO | 03091255 A1 | 11/2003 |
| WO | 2007126128 A1 | 8/2007 |
| WO | 2007126122 A1 | 11/2007 |
| WO | 2008133866 A1 | 11/2008 |

OTHER PUBLICATIONS

Wang et al., Radiosensitization of p53 Mutant Cells by PD0166285, a Novel G2 Checkpoint Abrogator, Cancer Research, vol. 61, pp. 8211-8217 (2001).

Palmer et al., Structure-activity relationships for 2-anilino-6-phenylpyrido[2,3-d]pyrimidin-7(8H)-ones as inhibitors of the cellular checkpoint kinase Wee1, Bioorganic & Medicinal Chemistry Letters, vol. 15, pp. 1931-1935 (2005).

(Continued)

*Primary Examiner* — Kendra D Carter (74) *Attorney, Agent, or Firm* — Yong Zhao; John C. Todaro (57) ABSTRACT

The instant invention relates to crystalline forms of MK-1775, an inhibitor of Wee1 kinase. Specifically, the instant invention relates to hemihydrates of MK-1775.

6 Claims, 6 Drawing Sheets

(56) References Cited

OTHER PUBLICATIONS

Molinari et al., Cell cycle checkpoints and their in activation in human cancer, Cell Proliferation, vol. 33, pp. 261-274 (2000).
McGowan et al., Human Wee1 kinase inhibits cell division by phosphorylating p34cdc2 exclusively on Tyr15, The EMBO Journal, vol. 12, No. 1, pp. 75-85 (1993).
Wang et al., Knockdown of Chk1, Wee1 and My11 by RNA Interference Abrogates G2 Checkpoint and induces Apoptosis, Cancer Biology & Therapy, vol. 3, No. 3, pp. 305-313 (2004).
U.S. Appl. No. 13/496,014, filed Mar. 14, 2012.

FIGURE 6

PREPARATION OF CRYSTALLINE FORMS OF DIHYDROPYRAZOLOPYRIMIDINONE

BACKGROUND OF THE INVENTION

The present invention relates to crystalline forms of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one (Compound A) or a salt thereof, which are useful in the field of treatment of various cancers as a kinase inhibitor, especially as a Wee1 kinase inhibitor.

Cells have a checkpoint mechanism such that, when the DNA therein is damaged, then the cells temporarily stop the cell cycle and repair the damaged DNA (Cell Proliferation, Vol. 33, pp. 261-274). In about a half of human cancers, a cancer-suppressor gene, p53 is mutated or depleted and thereby the cells have lost the G1 checkpoint function thereof. However, such cancer cells still keep the G2 checkpoint function remaining therein, which is considered to be one factor of lowering the sensitivity of the cells to DNA-active anticancer agents and to radiations.

A Wee1 kinase is a tyrosine kinase that participates in the G2 checkpoint of a cell cycle. Wee1 phosphorylates Cdc2 (Cdk1) tyrosine 15 that participates in the progress to the M stage from the G2 stage in a cell cycle, thereby inactivating Cdc2 and temporarily stopping the cell cycle at the G2 stage (The EMBO Journal, Vol. 12, pp. 75-85). Accordingly, in cancer cells having lost p53 function therein, it is considered that the G2 checkpoint function by Wee1 is important for repairing the damaged DNA so as to evade the cell death. Heretofore, it has been reported that the Wee1 expression reduction by RNA interference or the Wee1 inhibition by compounds may increase the sensitivity of cancer cells to adriamycin, X ray or gamma ray (Cancer Biology & Therapy, Vol. 3, pp. 305-313; Cancer Research, Vol. 61, pp. 8211-8217). From the above, it is considered that a Wee1 inhibitor may inhibit the G2 checkpoint function of p53-depleted cancer cells, thereby enhancing the sensitivity of the cells to DNA-active anticancer agents and to radiations.

Wee1 kinase inhibitors have been described in US Application 2005/0250836, WO2003/091255, Cancer Research, Vol. 61, pp. 8211-8217, or Bioorg & Med. Chem. Lett., Vol. 15, pp. 1931-1935. However, the compounds described in these references differ structurally from the compounds of the instant invention.

Compound A, its crystalline forms and salts thereof are described in International Publications WO2007/126128 (published on Nov. 8, 2007 to Merck & Co., Inc.), WO2007/126122 (published on Nov. 8, 2007 to Merck & Co., Inc.) and WO2008/133866 (published on Nov. 6, 2008, to Merck & Co., Inc.), which are hereby incorporated by reference in their entirety. Compound A has an excellent Wee1 kinase inhibitory effect and is useful in the treatment of cancer.

SUMMARY OF THE INVENTION

The instant invention relates to crystalline forms of Compound A, an inhibitor of Wee1 kinase. Specifically, the instant invention relates to hemihydrate Form I and hemihydrate Form II of Compound A.

DETAILED DESCRIPTION OF THE INVENTION

The invention provides novel crystalline forms of Compound A, an inhibitor of Wee1 kinase. Compound A, also known as MK-1775, is 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one, of structural formula:

Compound A which can be prepared by procedures described in International Publications WO2007/126128 and WO2007/126122, both of which published on Nov. 8, 2007 to Merck & Co., Inc. Other crystalline forms and salts of Compound A, including the monohydrate Form G and anhydrate Form B, are described in International Publication WO2008/133866, which published on Nov. 6, 2008, to Merck & Co., Inc., which is hereby incorporated by reference in its entirety.

The novel crystalline forms of Compound A or a salt thereof, especially the hemihydrates described herein, can be provided stably and constantly from the standpoint of the manufacturing process, and are useful in the treatment of cancer. The crystalline hemihydrate form I described herein is more stable thermodynamically than other known forms at temperatures up to 44° C. and relative humidity range of 14-93% (herein abbreviated as "RH"). The crystalline hemihydrate form II described herein is more stable thermodynamically than other known forms at temperatures equal or higher than 48° C. and relative humidity range of 19-93%. The relative stability of the hemihydrates and monohydrate Form G at relative humidity higher than 93% has been difficult to establish, because the solubility of the three crystalline forms are very close (difference <1 mg/mL) and the conversion is very slow.

Also, the hemihydrate Form II can be synthesized using a crystallization process that is more efficient and results in improved particle size and morphology control when compared to other forms The novel crystalline hemihydrate forms of Compound A, or a salt thereof, as well as Compound A per se, have a kinase-inhibitory effect, especially a Wee1 kinase-inhibitory effect, and are therefore useful as pharmaceutical agents for the treatment of various cancers such as brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma.

In particular, the novel crystalline forms of Compound A or a salt thereof, as well as Compound A per se, are useful as pharmaceutical agents, for example, for the treatment of breast cancer, lung cancer, pancreatic cancer, colon cancer, ovarian cancer, acute leukemia, chronic lymphatic leukemia, chronic myelocytic leukemia, Hodgkin's lymphoma.

The term "Compound A" as referred to herein means a compound of the above-described chemical structural formula and includes any amorphous form, polymorphic crystalline forms, hydrate, solvate and the mixture thereof.

X-ray powder diffraction studies are widely used to characterize molecular structures, crystallinity, and polymorphism. The X-ray powder diffraction pattern of the hemihydrate was generated on a Philips Analytical X'Pert PRO X-ray Diffraction System with PW3040/60 console. A PW3373/00 ceramic Cu LEF X-ray tube K-Alpha radiation was used as the source.

Figure 1:
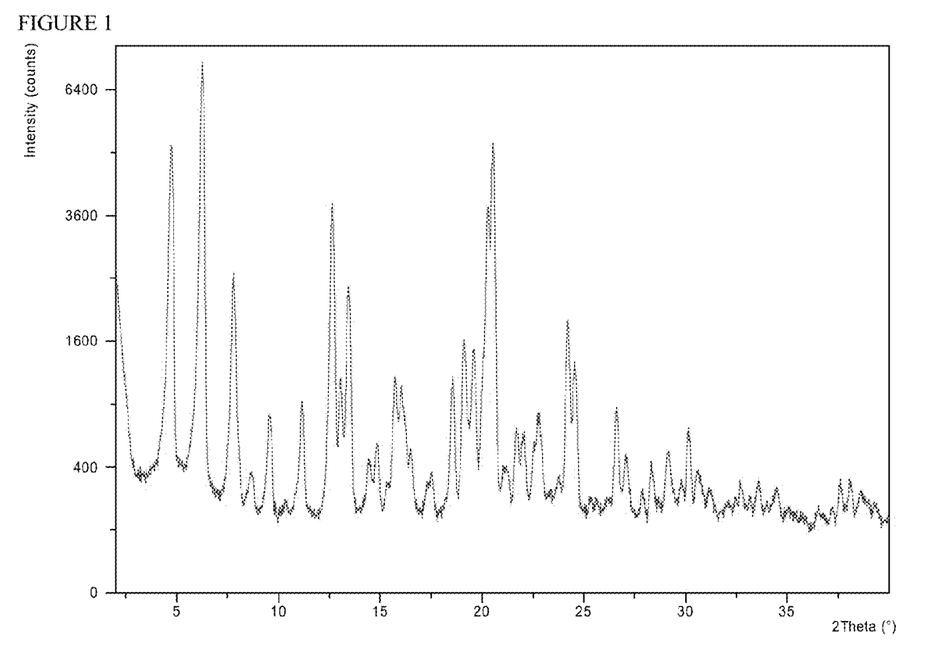
FIG. 1 is a characteristic X-ray diffraction pattern of the Crystalline Hemihydrate Form II of Compound A.

The X-ray powder diffraction pattern of the Hemihydrate Form II of Compound A is shown in FIG. 1. The Hemihydrate Form II of Compound A, also known as "the Hemihydrate Form II" or "the crystalline Hemihydrate Form II of Compound A," exhibits characteristic diffraction peaks corresponding to d-spacings of 13.81, 11.16, and 3.34 angstroms. The hemihydrate is further characterized by the d-spacings of 6.92, 6.74, and 6.53 angstroms. The hemihydrate is even further characterized by the d-spacings of 18.17 and 4.30 angstroms.

Figure 6:
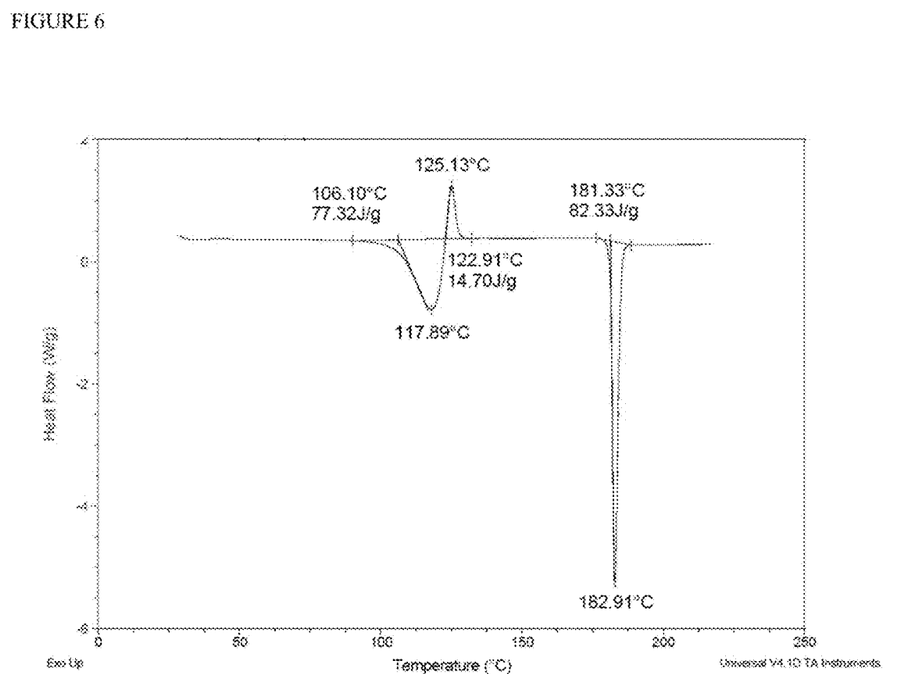
FIG. 6 is a typical DSC curve of the crystalline Hemihydrate Form I of Compound A.

The X-ray powder diffraction pattern of the Hemihydrate Form I of Compound A is shown in FIG. 6. The Hemihydrate Form I of Compound A, also known as "the Hemihydrate Form I" or "the crystalline Hemihydrate Form I of Compound A," exhibits characteristic diffraction peaks corresponding to d-spacings of 10.66, 5.30, and 4.18 angstroms. The hemihydrate is further characterized by the d-spacings of 9.11, 8.80 and 3.54 angstroms. The hemihydrate is even further characterized by the d-spacings of 18.22, 3.09 and 3.02 angstroms.

In addition to the X-ray powder diffraction patterns described above, the hemihydrates were further characterized by solid-state carbon-13 nuclear magnetic resonance (NMR) spectra. The solid-state carbon-13 NMR spectra were obtained on a Bruker DSX 400 WB NMR system using a Bruker 4 mm H/X CPMAS probe. The carbon-13 NMR spectra utilized proton/carbon-13 cross-polarization magic-angle spinning with variable-amplitude cross polarization, and TPPM decoupling at 80 kHz. The samples were spun at 10.0 kHz, and a total of 1024 scans were collected with a recycle delay of 5 seconds. A line broadening of 10 Hz was applied to the spectra before FT was performed. Chemical shifts are reported on the TMS scale using the carbonyl carbon of glycine (176.70 p.p.m.) as a secondary reference.

Figure 2:
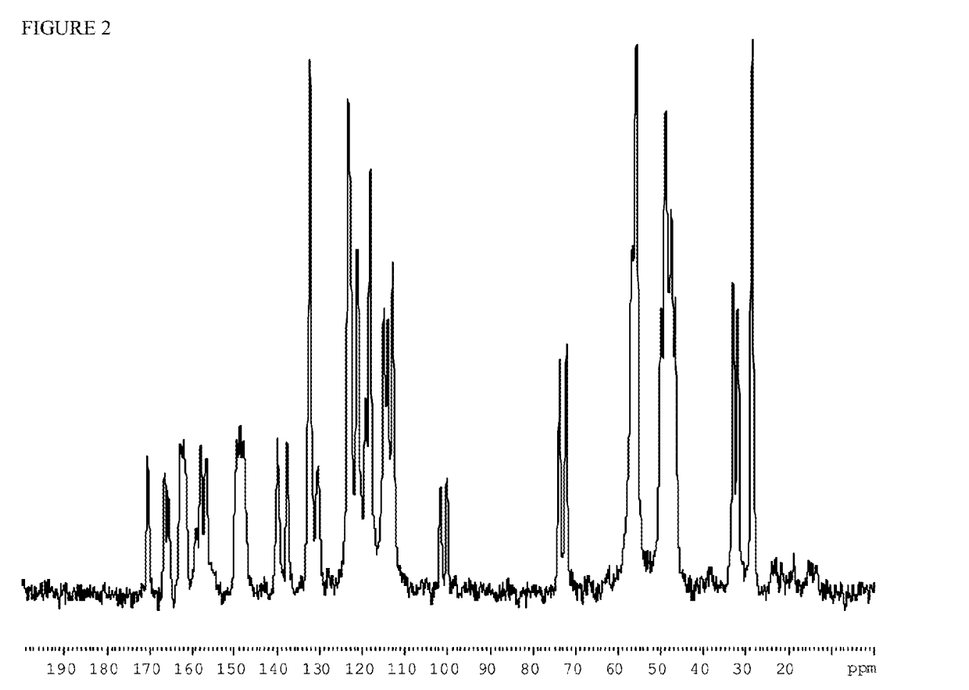
FIG. 2 is a carbon-13 cross-polarization magic-angle spinning (CPMAS) nuclear magnetic resonance (NMR) spectrum of the crystalline Hemihydrate Form II of Compound A.

The solid-state carbon-13 CPMAS NMR spectrum for the crystalline Hemihydrate Form II of Compound A is shown in FIG. 2. It is characterized by a solid-state carbon-13 CPMAS nuclear magnetic resonance spectrum showing signals at 28.6, 55.8 and 132.3 p.p.m. The spectrum is further characterized by signals at 123.2, 118.2, and 72.3 p.p.m.

Figure 5:
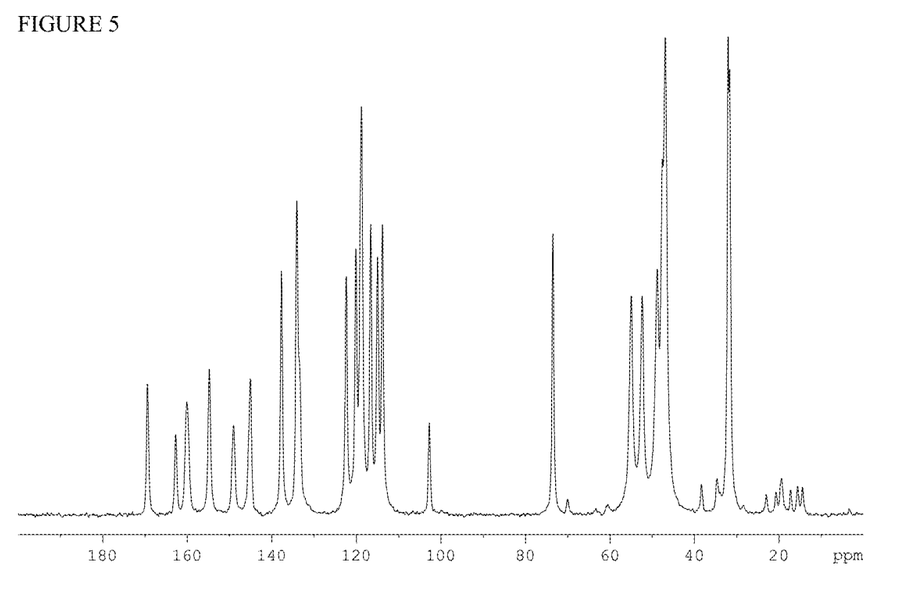
FIG. 5 is a carbon-13 cross-polarization magic-angle spinning (CPMAS) nuclear magnetic resonance (NMR) spectrum of the crystalline Hemihydrate Form I of Compound A.

The solid-state carbon-13 CPMAS NMR spectrum for the crystalline Hemihydrate Form I of Compound A is shown in FIG. 5. Crystalline Hemihydrate Form I is characterized by a solid-state carbon-13 CPMAS nuclear magnetic resonance spectrum showing signals at 116.6, 52.4, 55.0 and 31.7 p.p.m. The spectrum is further characterized by signals at 145.0, 154.8, 160.1 and 169.4 p.p.m.

DSC data are acquired using TA Instruments DSC 2910 or equivalent instrumentation. Between 1 and 7 mg sample are weighed into an open pan. This pan is then placed at the sample position in the calorimeter cell. An empty open pan is placed at the reference position. The calorimeter cell is closed and a flow of nitrogen was passed through the cell. The heating program is set to heat the sample at a heating rate of 10° C./min to a temperature of approximately 260° C. The heating program is started. When the run is completed, the data are analyzed using the DSC analysis program contained in the system software. The observed endotherms and exotherms are integrated between baseline temperature points that are above and below the temperature range over which these endotherms and exotherms are observed. The data reported are the onset temperature, peak temperature and enthalpy.

Figure 3:
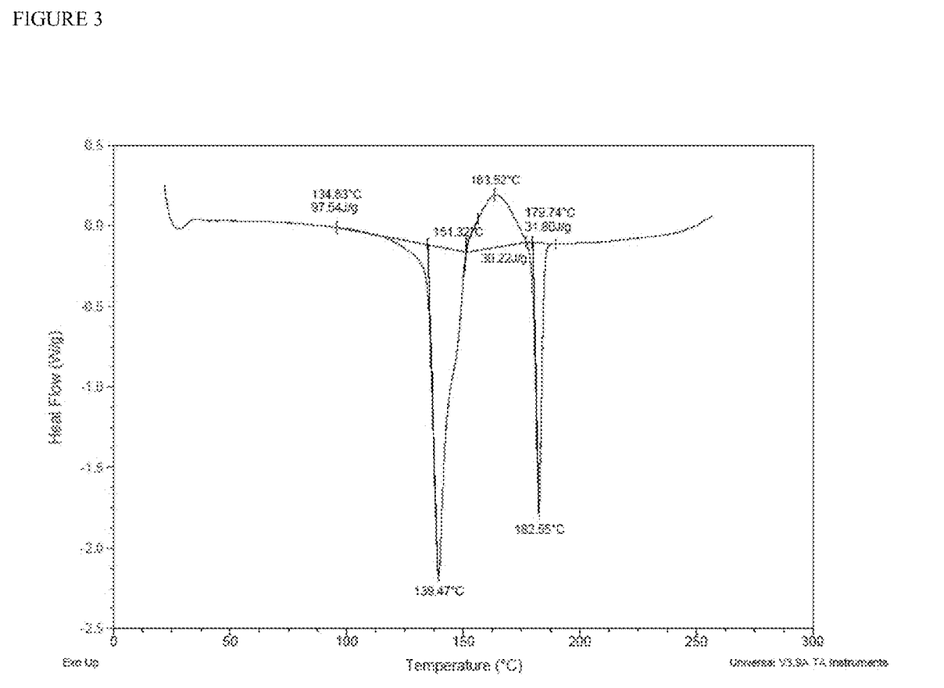
FIG. 3 is a typical DSC curve of the crystalline Hemihydrate Form II of Compound A.
Figure 4:
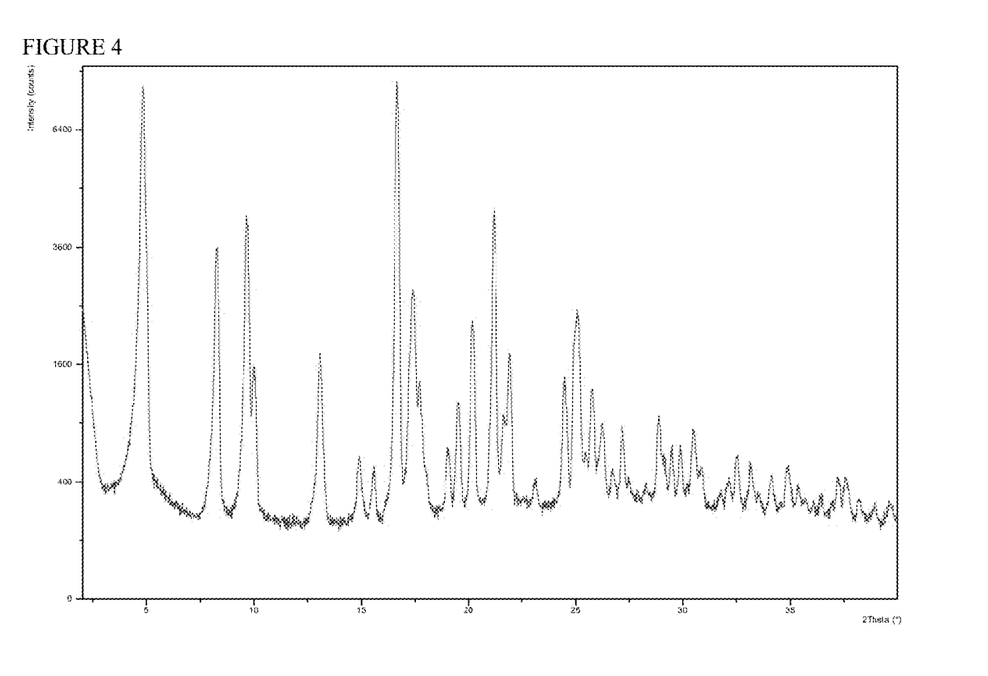
FIG. 4 is a characteristic X-ray diffraction pattern of the crystalline Hemihydrate Form I of Compound A.

The differential calorimetry scan for the crystalline Hemihydrate Form II of Compound A is shown in FIG. 3. The DSC curve is characterized by two endotherms and one exotherm. The first endotherm with an extrapolated onset temperature of 134.63° C., a peak temperature of 139.47° C. and enthalpy of 97.54 J/g is associated with the loss of water from the crystal lattice. The loss of water leads to a formation of amorphous phase, which re-crystallizes as the anhydrate Form B of Compound A. The re-crystallization is observed in the DSC curve as an exotherm with an extrapolated onset temperature of 151.32° C., a peak temperature of 163.52° C. and enthalpy of 30.22 J/g. The second endotherm, with an extrapolated onset temperature of 179.74° C., a peak temperature of 182.55° C. and enthalpy of 31.8 J/g is due to the melting of the Anhydrate Form B of Compound A.

The differential calorimetry scan for the crystalline Hemihydrate Form I of Compound A is shown in FIG. 6. The DSC curve is characterized by two endotherms and one exotherm. The first endotherm with an extrapolated onset temperature of 106.1° C. and a peak temperature of 117.9° C. is associated with the loss of water from the crystal lattice. The loss of water leads to a formation of amorphous phase, which re-crystallizes as the Anhydrate Form B of Compound A. The re-crystallization is observed in the DSC curve as an exotherm with an extrapolated peak temperature of 125.1° C. The second endotherm, with an extrapolated onset temperature of 181.3° C., a peak temperature of 182.9° C. and enthalpy of 82.33 J/g is due to the melting of the Anhydrate Form B of Compound A.

The compounds of the present invention can be prepared according to the following specific examples. Those skilled in the art will readily understand that known variations of the conditions and processes of the following preparative procedures can be used to prepare these compounds. All temperatures are degrees Celsius unless otherwise noted.

EXAMPLE 1

PREPARATION OF HEMIHYDRATE FORM II OF COMPOUND A

Compound A Monohydrate Form G
MW: 518.6 as monohydrate
MW: 500.6 as free

Compound A Hemihydrate Form II
MW: 509.6 as hemihydrate
MW: 500.6 as free

| Materials | M.W. | Amount | mol | eq. |
| --- | --- | --- | --- | --- |
| Compound A Monohydrate Form G | 518.6 | 32 g | 0.0617 | 1.00 |
| NMP (d = 1.028) | 99.1 | 106.7 mL | | |
| $H_2O$ (d = 1.000) | 18.01 | 319.7 mL | — | — |
| 1:3 (v:v) NMP:DIW | | 64 mL | | |
| 2:5 (v:v) EtOH:DIW | | 64 mL | | |
| Compound A Hemihydrate Form II (Seed) | 509.6 | 0.64 g | 0.0013 | 2.04 |

To a 500 mL jacketed vessel with overhead agitation is charged 32 g Compound A Monohydrate Form G and 106.7 mL N-Methyl-2-pyrrolidone (NMP). The mixture is stirred and heated to 50° C. To this solution is added 35.7 mL $H_2O$. The batch is then seeded with 0.64 g Compound A Hemihydrate Form II. The batch is aged for 15 minutes. To this slurry is then added 91 mL $H_2O$ over 7 hours via syringe pump, followed by 193 mL over 5 hrs. The batch is then cooled from 50° C. to 20° C. over three hours. After the cooldown, the batch is IKA milled (~30 turnovers).

The batch is then filtered, washed with 64 mL 1:3 (v:v) NMP:DIW and then 64 mL 2:5 (v:v) EtOH:DIW. The batch is dried in a vacuum oven at 35° C. Compound A Hemihydrate Form II (~30.5 g) was obtained as a yellow solid in a yield of approximately 95%.

EXAMPLE 2

PREPARATION OF HEMIHYDRATE FORM II OF COMPOUND A

Compound A
IPA solvate

Compound A
Hemihydrate Form II

| Raw Material Name | MW | Charge Amount (kg) | Moles | Eq/vol |
| --- | --- | --- | --- | --- |
| Compound A IPA Solvate (~17.5 wt % IPA, Free-Base Used as Basis) | 500.95 | 37.8 | | 1.00 eq |
| Butylated Hydroxytoluene (BHT) | 220.4 | 0.0143 | 0.064 | 150 PPM in NMP |
| N-Methyl-2-pyrrolidone (NMP) | 99.13 | 95.31 | | 3.0 L/kg freebase |
| Deionized water (DIW) | 18 | 215.3 | | 7 L/kg freebase |
| 3:1 DIW:NMP | | ~70 L | | 2.25 L/kg freebase |
| 9:1 DIW ETOH | | ~150 L | | 4.5 L/kg freebase |
| 9:1 DIW ETOH | | ~150 L | | 4.5 L/kg freebase |
| Compound A Hemihydrate (Form II) Seed (~1.8% water) | 500.95 | ~0.62 | | 2% Seed Load |

N-Methyl-2-pyrrolidone (NMP) with 150 PPM BHT (2.0 L/kg) and Compound A IPA Solvate (1.0 eq.) are charged to the reaction vessel. After all solids have dissolved, NMP with 150 PPM BHT (1.0 L/kg) is charged to rinse down the vessels/equipment. The vessel is heated to 60 C and DIW is charged slowly to the solution until DIW content is 32 vol % DIW (~1.3 L/kg, 32 vol % relative to NMP). The seed (~2 wt %) is charged. The seed port is rinsed with 50 vol % NMP in DIW. The seed bed is aged for 1 hour. Once seed bed is established, DIW is charged slowly and the water content is brought to 50 vol % over at least 2 hours (~1.7 L/kg). The remaining DIW is charged slowly to the batch over 2 hours. The final water concentration should be 70 vol % (~3.98 L/kg, Total water addition ~7 L/kg). Terminal IKA milling at T>50° C. for ~30 Turnovers is used to reduce particle size. If a significant number of fine particles are generated, a heat-cool cycle is performed. The heat cool cycle consists of heating the batch to 80° C. over 4 hours, holding at 80° C. for 4 hours, and cooling to 50° C. over 4 hours. The batch is filtered at temperature equal or higher than 50° (T≥50° C.). Displacement wash was performed on the batch with hot (T≥50° C.) 75% DIW:25% NMP (v:v) (2.0 L/kg freebase). The displacement wash is filtered. Slurry wash of the batch is performed with hot (T≥50° C.) 90% DIW:10:EtOH (v:v) (2.0 L/kg freebase) and the slurry is filtered. The washing procedure was repeated with the same amount of hot 90% DIW:10:EtOH (v:v). To avoid cake dehydration, the batch is humid dried at 65° C.

EXAMPLE 3

PREPARATION OF HEMIHYDRATE FORM I OF COMPOUND A

Compound A Hemihydrate Form II
MW: 509.6 as hemihydrate
MW: 500.6 as free

Compound A Hemihydrate Form I
MW: 509.6 as hemihydrate
MW: 500.6 as free

| Materials | M.W. | Amount | mol | eq. |
|---|---|---|---|---|
| Compound A Hemihydrate Form II | 518.6 | 60 g | 0.118 | 1.00 |
| BHT | 220.4 | 33 mg | | |
| NMP (d = 1.028) | 99.1 | 180 mL | | |
| H$_2$O (d = 1.000) | 18.01 | 480 mL | — | — |
| 2:5 (v:v) EtOH:DIW | | 350 mL | | |
| Compound A Hemihydrate Form I (Seed) | 509.6 | 1.2 g | 0.0013 | 0.02 |

To a 2 L RB flask with overhead agitation is charged 60 g Compound A Hemihydrate Form II and 180 mL N-Methyl-2-pyrrolidone (NMP). The mixture is stirred and heated to 45° C. to dissolve. The batch is cooled to 40° C. To this solution is added 60 mL H$_2$O over 30 min. The batch is then seeded with 1.2 g Compound A Hemihydrate Form I. To this slurry is then added 114 mL H$_2$O over 2.5 hours, followed by 306 mL over 2.5 hrs. The batch is then cooled from 40° C. to 20° C. After the cooldown, the batch is high shear rotor-stator wetmilled to reduce the particle size.

The batch is then filtered, washed with ~350 mL 2:5 (v:v) EtOH:DIW. The batch is dried with vacuum and N$_2$ stream at room temperature (~20° C.). Compound A hemihydrate Form I (53.1 g) was obtained as a light yellow solid in a yield of approximately 90%.

In addition to a mixture of hemihydrates, any other crystalline form of Compound A free base can be used as a starting material for preparation of hemihydrate Form I.

What is claimed is:

1. A novel crystalline 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one hemihydrate which is characterized by an x-ray powder diffraction pattern, collected using copper Kα radiation, corresponding to d-spacings of 10.66, 5.30 and 4.18 angstroms.

2. The novel crystalline hemihydrate of claim 1 which is further characterized by d-spacings of 9.11, 8.80 and 3.54 angstroms.

3. The novel crystalline hemihydrate of claim 2 which is further characterized by d-spacings of 18.22, 3.09 and 3.02 angstroms.

4. The novel crystalline hemihydrate of claim 1 which is characterized by a solid-state carbon-13 CPMAS nuclear magnetic resonance spectrum showing signals at 116.6, 52.4, 55.0 and 31.7 p.p.m.

5. The novel crystalline hemihydrate of claim 4 which is further characterized by signals at 145.0, 154.8, 160.1, and 169.4 p.p.m.

6. A pharmaceutical composition comprising the crystalline hemihydrate of claim 1 and a pharmaceutically acceptable carrier.

* * * * *